United States Patent [19]

Pratt

[11] Patent Number: 5,573,002
[45] Date of Patent: Nov. 12, 1996

[54] METHOD AND APPARATUS FOR MEASURING INTERNAL TISSUE CHARACTERISTICS IN FEED ANIMALS

[75] Inventor: William C. Pratt, Canyon, Tex.

[73] Assignee: Micro Chemical, Inc., Amarillo, Tex.

[21] Appl. No.: 395,931

[22] Filed: Feb. 27, 1995

[51] Int. Cl.$^6$ ..................................................... A61B 8/00
[52] U.S. Cl. ...................................................... 128/660.07
[58] Field of Search .......................... 128/660.02, 660.03, 128/660.06, 660.07, 662.03; 73/644

[56] References Cited

U.S. PATENT DOCUMENTS

| | | | |
|---|---|---|---|
| 4,359,055 | 11/1982 | Carlson ................................... | 128/660 |
| 4,359,056 | 11/1982 | Carlson ................................... | 128/660 |
| 4,844,080 | 7/1989 | Frass et al. ........................... | 128/662.03 |
| 5,079,951 | 1/1992 | Raymond et al. ................... | 128/660.07 |
| 5,218,963 | 6/1993 | Mazess ................................. | 128/660.06 |
| 5,303,708 | 4/1994 | Stouffer ............................... | 128/660.07 |
| 5,353,796 | 10/1994 | Schroeder et al. .................. | 128/660.01 |

*Primary Examiner*—George Manuel
*Attorney, Agent, or Firm*—Klarquist Sparkman Campbell Leigh & Whinston, LLP

[57] ABSTRACT

An ultrasonic apparatus for evaluating internal tissue characteristics in livestock is described. The apparatus comprises a reservoir containing a conductive liquid, an ultrasonic transducer, and a handpiece which is liquidly coupled to the reservoir. As with any electronic apparatus, the apparatus of the present invention can be controlled by one or more computers. The handpiece may further comprise a dispenser for dispensing conductive liquid from the reservoir and onto the livestock. A liquid pump is liquidly connected to both the conductive liquid reservoir and the dispenser. The apparatus also preferably includes a switch unit that is liquidly coupled to the pump and the dispenser, and electrically coupled to the transducer and the computer. The switch unit includes at least a liquid switch for actuating the pump and a transducer switch for actuating the transducer. A method for measuring internal tissue characteristics using the apparatus also is described. The ultrasound transducer is positioned on an animal's hide so that the transducer is substantially focused on a rib-eye muscle. Conductive liquid, such as water, vegetable oil or mineral oil, is dispensed from the reservoir through the dispenser and onto the hide by actuating the pump. An ultrasound image is then obtained by actuating the transducer.

25 Claims, 3 Drawing Sheets

METHOD AND APPARATUS FOR MEASURING INTERNAL TISSUE CHARACTERISTICS IN FEED ANIMALS

FIELD OF THE INVENTION

This invention concerns an ultrasound measuring device for measuring internal tissue characteristics, such as backfat, marbling and muscle in livestock.

BACKGROUND OF TEE INVENTION

Feedlots promote animal growth and improve the quality of the animal prior to slaughter. Although some feedlots are designed to handle relatively few cattle, most of the feedlots in North America are considerably larger and accommodate thousands of animals. There is considerable diversity in individual animal characteristics, such as weight, frame size, fat content, fat deposition rate, intramuscular fat (marbling) and muscling within this feedlot cattle population. The producer's goal in using a feedlot is to optimize the growth rate and food value characteristics of each animal prior to slaughter. Achieving this goal ideally requires obtaining physical data and growth characteristics for each animal at multiple times during its stay in the feedlot.

Some of these measurements have been made using probe-like instruments. For instance, backfat has been measured by piercing the skin of the animal and taking physical measurements. This clearly aggravates the animal and may be illegal in certain areas. See Carlson's U.S. Pat. Nos. 4,359,055 and 4,359,056. Ultrasound techniques have been developed to replace these physically invasive and time-consuming methods. Ultrasonic devices transmit ultrasonic waves into the animal. Ultrasonic waves are transmitted and reflected by muscle tissue differently than by fat. As a result, the reflection of ultrasonic waves can determine certain meat characteristics, including the depth of various fat layers by determining fat boundaries or fat/tissue boundaries.

The meat producing industry has tried to use ultrasound devices for years to efficiently measure internal tissue characteristics. See, for instance, Carlson's patents which describe an ultrasonic digital backfat meter that was designed primarily for use with swine. Known devices have proven inefficient for monitoring large numbers of cattle. Measuring each animal takes too much time, and often the results are inaccurate. The speed of the measurement depends on several factors. For instance, cattle have relatively thick hair compared to other food producing animals, such as swine, which decreases ultrasonic conductivity. In order to obtain an acceptable signal, operators often clip the cattle's hair close to the skin before the ultrasound device is placed in contact therewith. This takes time and is impractical for feedlots in which many hundreds or thousands of animals must be measured, sometimes more than once, during their residency in the feedlot. When a proper conductive contact between the device and the animal is not achieved, a poor image of internal fat and muscle tissues is obtained. It is not possible to accurately measure tissue dimension or texture characteristics under such conditions.

Operators have tried spraying a conductive liquid onto the animal using a squirt bottle immediately prior to placing ultrasonic devices in contact with the animal so as to eliminate the need for hair clipping. This also has proven ineffective for large feed lots. Manipulating both the ultrasound device and the squirt bottle is inconvenient, and the time required to apply the liquid adds significantly to the processing time.

Another drawback associated with known devices is that the controls are not integrated at the fingertips of a single operator. More than one operator may be required to operate the device. Alternatively, a single operator may have to reset and reposition the ultrasound device after each animal is tested by moving to a location remote from the testing site where the computer is located. As a result, known ultrasonic techniques take as long as 120 seconds to measure each animal. While this may not seem like a significant amount of time, it is considerably too long when thousands of animals must be processed daily.

SUMMARY OF THE INVENTION

A primary objective of this invention is to overcome the deficiencies of the prior art ultrasound measurement apparatuses and methods for use in measuring tissue characteristics in animals, and to provide an apparatus and method that will measure quickly, easily and accurately compared to prior such apparatuses and methods.

Another specific objective of this invention is to integrate ultrasound transmission, conductive liquid dispensation and ultrasound reading functions so that the control of all functions can be placed at the fingertips of a single operator.

Another object of this invention is to provide an applicator device that includes both an ultrasound transducer and a conductive liquid dispenser.

In general, the invention seeks to fulfill these and other objectives by providing a reservoir containing a conductive fluid, an ultrasonic transducer, and a handpiece which is fluidly connected to the reservoir. A particular embodiment of the invention comprises an ultrasonic transducer and, preferably, a hand-held handpiece for movably positioning the ultrasonic transducer adjacent to or in contact with the skin of livestock. The handpiece further comprises a built-in fluid passage and dispenser for dispensing fluid from the conductive fluid reservoir onto the livestock. A fluid pump may be fluidly coupled to both the reservoir and the dispenser in the handpiece using flexible tubing, such as TIGON tubing, so that fluid can be pumped from the reservoir to the handpiece dispenser. A computer also is used with the apparatus, and is operatively coupled to the transducer.

The apparatus may further include a hand-held switch unit that is electrically and fluidly coupled to the pump and the dispenser, and electrically or otherwise operably coupled to the transducer and the computer. The switch unit includes at least a fluid switch for actuating the pump and a transducer switch for actuating the computer reading of the image produced by the transducer. The switch unit may further include a computer switch electrically coupled to the computer for actuating computer functions such as recording an ultrasound reading from the transducer. In other words, with the switch unit a single operator can control all the components of the invention, including remotely positioned pumps and computers, by actuating an appropriate switch housed in the hand-held switch unit.

A preferred embodiment of the invention includes at least one computer which acts to control the transducer and evaluate and record data. A video and/or computer monitor may be electrically coupled to the transducer and the computer. The monitor is positioned so that the operator can view the ultrasound image during the measuring process. This allows the operator to obtain a clear ultrasound image before commanding the computer, via the hand-held switch unit, to record data, such as backfat, marbling, and muscle measurements from the ultrasound image. The apparatus can be used in combination with an overall cattle management system such as might be found in a feedlot to sort cattle, promote feed efficiency, and optimize shipping dates for animals, either individually or in groups.

The present invention also provides an improved method for measuring internal tissue characteristics in livestock at established and accepted locations on the animal. For example, with cattle the method comprises first providing an internal tissue characteristic evaluation apparatus substantially as described above. The ultrasound transducer typically is positioned on an animal's hide. The transducer preferably is positioned so that it is substantially focused on an area over the rib-eye muscle between rib 12 and 13. This is a location widely accepted for making measurements for grading and evaluating the animal with respect to internal tissue characteristics. The position of the ultrasound transducer relative to the backbone of each animal can be optimized by moving the transducer within the handpiece. This allows the apparatus to optimally evaluate livestock of different sizes. Conductive fluid is dispensed from the reservoir through the dispenser and onto the hide. This can be accomplished by actuating the pump. Virtually any conductive fluid will work, as long as it increases the ultrasonic conductivity and is not toxic to the livestock. Soley by way of example, conductive fluids useful for the invention may be selected from the group consisting of water, vegetable oil and mineral oil. A sufficient amount of the conductive fluid, such as less than about 50 milliliters, and more typically about 30 milliliters, is dispensed onto the animal's hide to increase the ultrasonic conductivity. An operator monitors the ultrasound monitor until a clear image is seen. The ultrasound image is then analyzed by the computer using commercially available software, and the data concerning internal tissue characteristics is recorded.

DETAILED DESCRIPTION OF THE PREFERRED EMBODIMENTS

The present apparatus is especially suitable for use at feedlots for measuring particular meat characteristics of large numbers of livestock. It therefore will be apparent that the apparatus can be used in combination with other livestock measuring systems for measuring other animal characteristics. The apparatus has been designed so that dispensing the conductive fluid, taking accurate measurements, recording the data and resetting the computer takes less than about 30 seconds, and more typically about 15 seconds, for each animal. Although the present invention can be used to measure meat characteristics of many species, it is particularly useful for measuring backfat, intramuscular fat and muscle of cattle.

I. ULTRASOUND APPARATUS

Figure 1:
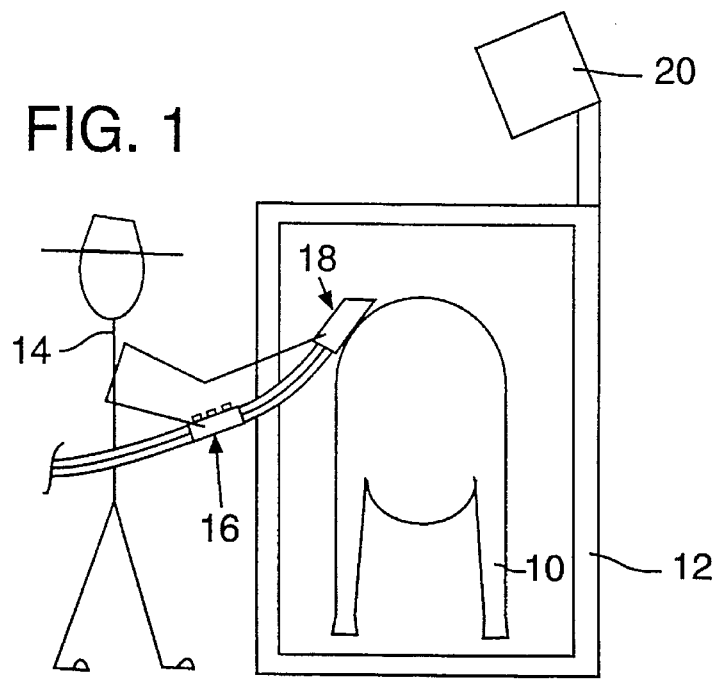
FIG. 1 is a schematic view illustrating the use of an embodiment of the ultrasound apparatus and method of the present invention in a typical animal measuring situation.

FIG. 1 shows a feed animal 10 positioned in a feedlot stall 12. Adjacent the stall is an operator 14. Operator 14 holds and operates both the switch unit 16, as well as the handpiece 18, of the present apparatus. Operator 14 also can view ultrasound images on monitor 20 during the measurement process.

A. Electric and Fluid Line Connections

Figure 2:
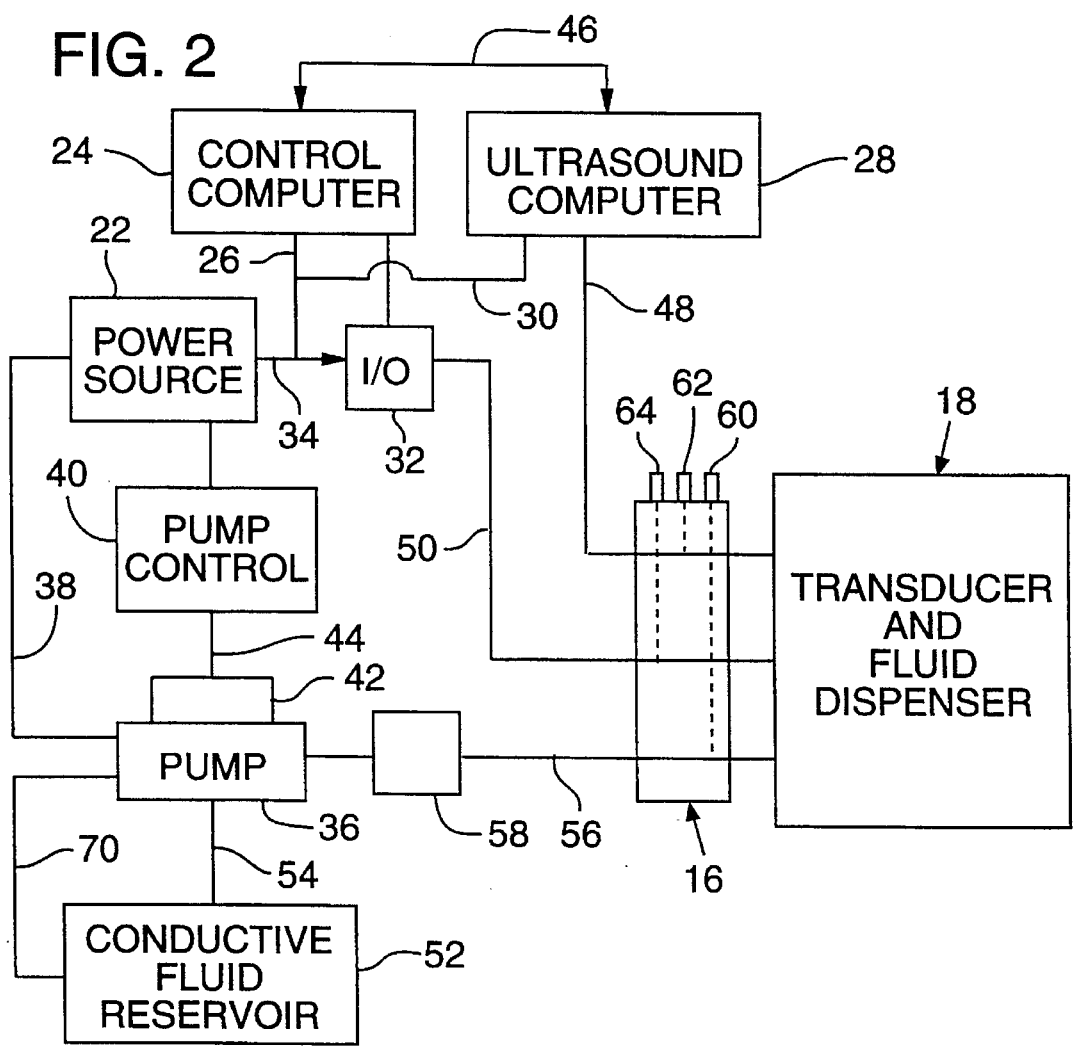
FIG. 2 is a schematic diagram showing a complete system of one embodiment of an apparatus according to the present invention.

FIG. 2 is a block diagram which illustrates certain components for an embodiment of the present invention. FIG. 2 also illustrates certain fluid and electric interconnections between these components. Power source 22 is electrically coupled to each unit requiring power. More specifically, power source 22 is electrically coupled to control computer 24 by cable 26, to ultrasound computer 28 by cable 30, to input/output module 32 by cable 34, and to pump 36 using cable 38. Pump 36 is controlled by pump control 40, which is electrically coupled to a three-way solenoid valve 42 by cable 44. A data cable 46 interconnects control computer 24 and ultrasound computer 28. FIG. 2 also illustrates that the ultrasound computer 28 is electrically coupled to switch unit 16 by cable 48. Input/output module 32 also is electrically coupled to the handpiece 18 by cable 50.

Pump 36 is fluidly coupled to reservoir 52, which contains a conductive fluid, by fluid conduit 54. Pump 36 is further fluidly coupled to switch unit 16 by fluid line 56. As shown in FIG. 2, a quick disconnect 58 may be placed in fluid line 56. This quick disconnect 58 is provided solely for convenience, and allows the pump fluid line 56 to be quickly disconnected from handpiece 18.

Each of the individual lines, namely electric cables 48, 50, and fluid line 56, are interfaced with the handpiece 18 by switch unit 16. Each of the components of the apparatus can be individually actuated using the switches 60, 62 and 64 on switch unit 16. Thus, by depressing the appropriate switch, each function of the apparatus can be actuated.

B. Components of the Preferred Embodiment

The components of the apparatus mentioned above will now be described in more detail. Power source 22 is a conventional piece of equipment that can be obtained commercially. Virtually any power source now known or hereafter developed that can safely power sensitive electronic apparatuses can be used to practice the invention.

Control computer 24 also is a conventional piece of equipment, and any computer which has sufficient capability to control and interface with ultrasound computer 28 will suffice. One example, without limitation, of a control computer 24 suitable for this operation is an IBM PC. Control computer 24 controls certain functions of the ultrasound computer 28. Commercial software is available for operating the control computer 24 to control ultrasound computer 28. One example of software suitable for this operation is sold by Animal Ultrasound Services, Inc., of Ithaca, N.Y.

The present apparatus operates by generating and transmitting into livestock an ultrasound energy pulse. This energy pulse is produced and controlled by ultrasound computer 28 and ultrasound transducer 66. Each of these components can be purchased. One example of an ultrasound apparatus that can be used to practice the invention is an ALOKA 500 V Ultrasound Computer. The ALOKA 500 V is purchased in combination with an ultrasound transducer 66 and transducer cable 68 for coupling the transducer 66 to the computer 28.

Input/output module 32 controls the signals input to and from computer 24 and to the components housed in handpiece 18. Again, the I/O module 32 is a conventional piece of equipment, and virtually any input/output module 32 will suffice for this invention. One prototype of the invention was assembled using an OPTO 22 I/O board. The OPTO 22 I/O board includes: a 1AC5Q input module; a PB16HQ circuit board; a B1 brainboard; a PBSA PP/S power supply; and an OAC5Q output module.

A pump 36 pumps conductive liquid to handpiece 18. The conductive liquid is contained in reservoir 52. Any conductive liquid likely will work for the present invention. The selection of a suitable conductive liquid will best be decided by considering, inter alia, the conductivity of the liquid, the expense of the liquid, the availability of the liquid and the toxicity of the liquid. Solely by way of example, suitable conductive liquids may be selected from the group of conductive liquids consisting of water, vegetable oil and mineral oil. Pump 36 is liquidly connected to conductive liquid reservoir 52 using liquid conduit 54, which was made from flexible TIGON tubing. A pressure equalization tube 70, also made from TIGON tubing, couples the liquid reservoir 52 and the pump 36. Pressure equalization tube 70 equalizes the pressure between the pump 36 and the reservoir 52 when the pump 36 is not in operation. This helps prevent liquid leaks from reservoir 52.

Conductive liquid is dispensed from reservoir 52 upon actuation of the pump 36. Liquid dispensation is controlled by a three-way solenoid valve 42, which is electrically coupled to pump control 40. Three-way valve 42 can be electrically actuated by switch 60, which is housed in switch unit 16. This dispenses conductive liquid from reservoir 52 through liquid conduits 54 and 56 to handpiece 18. When the pump 36 is not in use, the solenoid valve is open to pressure equalization tube 70 to equalize the pressure between the pump 36 and reservoir 52. Liquid back flow from handpiece 18 can be checked by a check valve 72, which is mechanically coupled to the handpiece 18.

Figure 3:
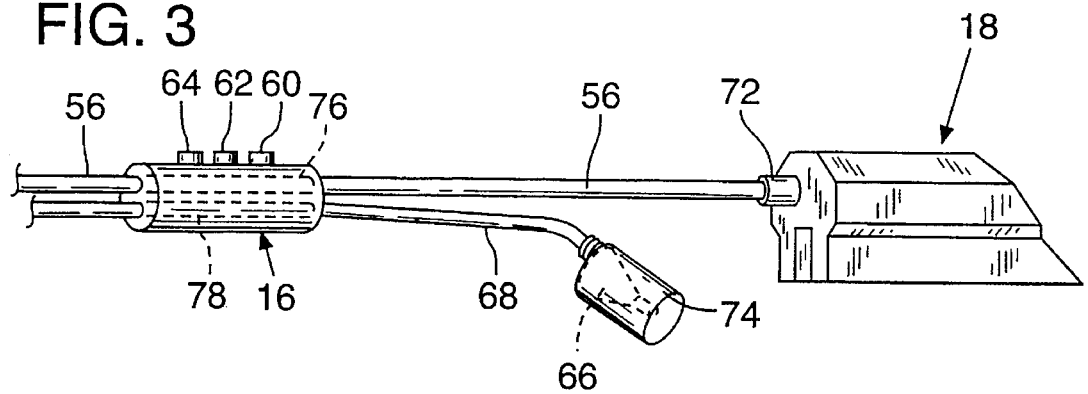
FIG. 3 is a side, partially disassembled view, illustrating the ultrasound transducer and dispensing handpiece unit of the invention.

FIG. 3 is a schematic diagram of the switch unit 16, handpiece 18, cables 48, 50, and liquid conduit 56. FIG. 3 shows transducer 66 separated from handpiece 18. FIG. 3 further shows that ultrasound transducer 66 is surrounded by a clear protective housing 74. Housing 74 performs at least two functions. First, housing 74 protects ultrasound transducer 66 from contact damage. Furthermore, protective housing 74 facilitates the positioning of transducer 66 in handpiece 18 as described below. The protective housing 74 in a prototype illustrated in FIG. 3 was made from TIGON tubing sized to tightly receive transducer 66 therein.

Figure 4:
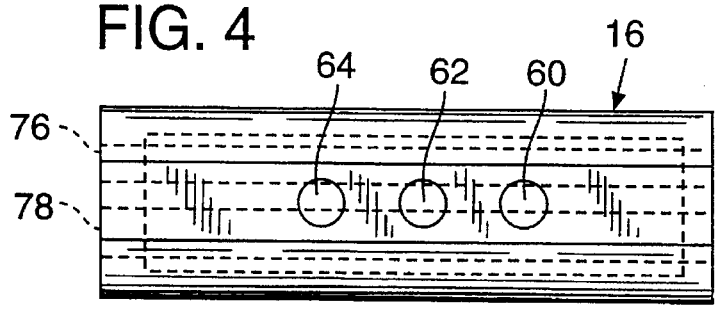
FIG. 4 is a plan view of the switch unit illustrated in FIG. 3.
Figure 5:
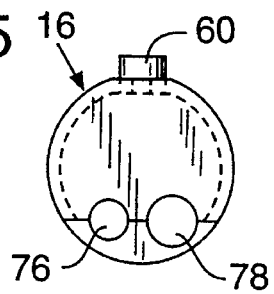
FIG. 5 is a front end view of the switch unit of FIG. 4.
Figure 9:
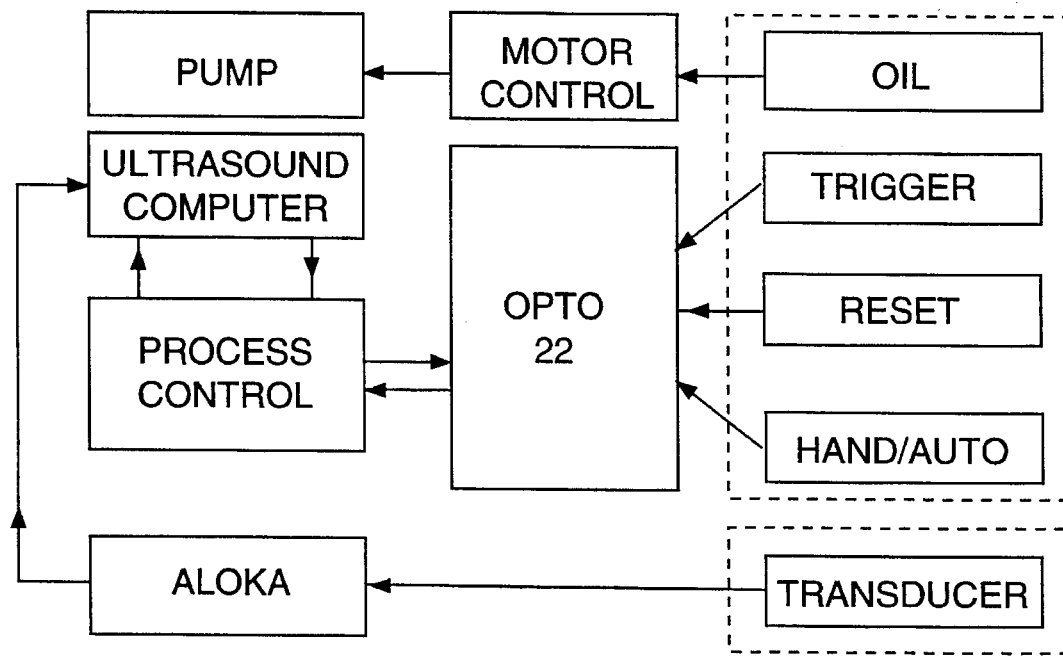
FIG. 9 is a schematic illustrating the switch unit of FIG. 4.

FIG. 4 is a schematic top plan view and FIG. 5 is an end view illustrating switch unit 16. In a prototype, switch unit 16 was made from a polypropylene block that was machined to include passages 76 and 78 therethrough. Conduit 76 provides a passage through switch unit 16 for liquid line 56. Passage 78 provides a passage through switch unit 16 for electric cables 48 and 50. Switch unit 16 includes three switches 60, 62 and 64. The switches include conductive liquid switch 60, trigger switch 62 for commanding the computer to read and analyze the image, and reset switch 64 for clearing a previous reading to prepare for rereading an animal or reading a new animal. These switches and their functions also are illustrated in FIG. 9. Switch 60 actuates liquid pump 36 so that conductive liquid from reservoir 52 is pumped through liquid line 56 and into handpiece 18. The amount of time that pump 36 operates is governed by a timer switch on pump 36 (not shown). Thus, by actuating switch 60, pump 36 is induced to pump conductive liquid from reservoir 52 for the period of time allowed by the timer switch on the pump. In a current prototype, the pump 36 is actuated for a period of less than about 5 seconds, and typically about 3 seconds, during which time less than about 50 milliliters, and more typically about 30 milliliters, is pumped from reservoir 52 to the handpiece 18.

A second switch 62 is electrically coupled to the ultrasound computer 28 by cable 48. Switch 62 activates the computer 28 to read and analyze the ultrasound image that is produced by transducer 66 as displayed on monitor 20. Thus, once the transducer 66 is correctly positioned, operator 14 depresses switch 62 to cause the computer 28 to read the ultrasound image.

A third switch 64 also is provided on switch unit 16. Switch 64 is a reset switch electrically coupled to input/output module 32 by cable 50. Switch 64 is depressed by operator 14 when the image has been read by computer 28 or when the operator wants to discard a previous reading and record a new reading of a given animal's image. This can include reapplying conductive liquid from the handpiece 18 onto the animal. This resets the computer 24 and input/output module 32 for receiving new information from a different animal 10.

Figure 6:
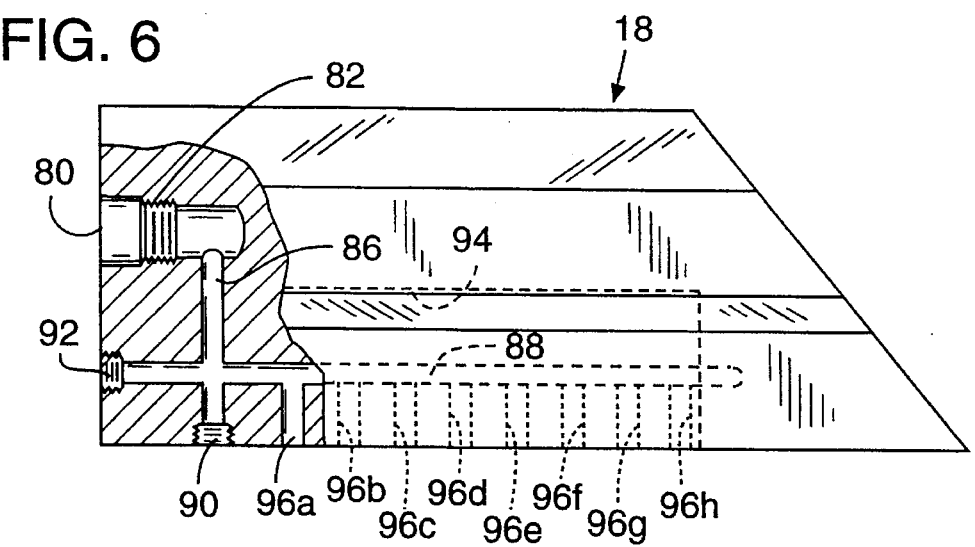
FIG. 6 is an enlarged side view of the handpiece illustrated in FIG. 3.
Figure 7:
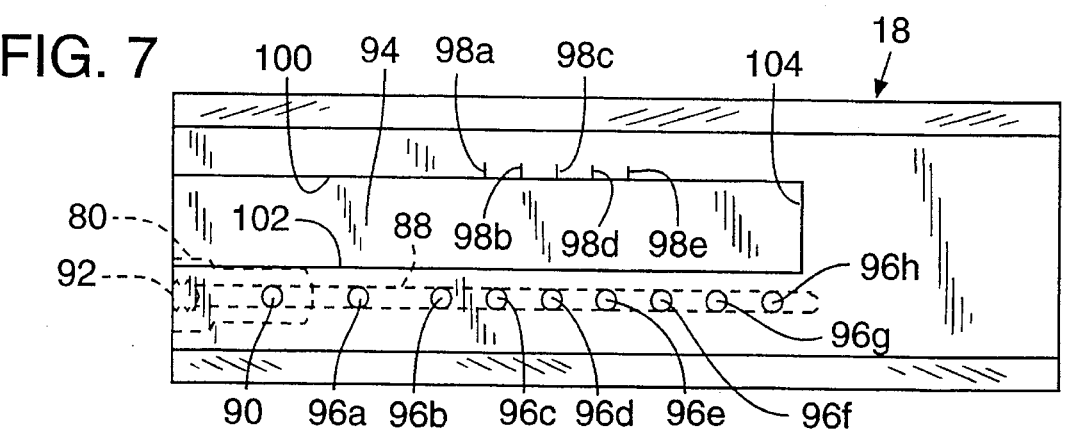
FIG. 7 is a bottom plan view of the handpiece of FIG. 3.
Figure 8:
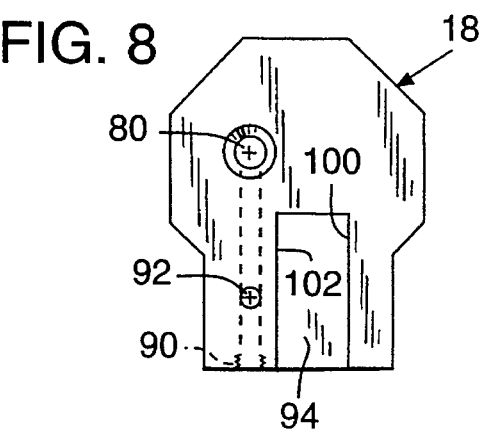
FIG. 8 is a rear end view of the handpiece illustrated in FIG. 3.

FIGS. 6–8 further illustrate the construction of handpiece 18. FIG. 6 is a side schematic view of the housing 18. Housing 18 is manufactured for this particular application, and can be manufactured from a number of suitable materials. The embodiment of a prototype illustrated in FIGS. 6–8 was manufactured from polypropylene. A block of polypropylene having suitable dimensions was obtained and then machined to have substantially the appearance illustrated in FIGS. 6–8.

More particularly, handpiece 18 is machined to include a threaded inlet 80 for receiving liquid line 56. Any suitable means for coupling the liquid line 56 to housing 18 will suffice. FIGS. 6–8 illustrate a male threaded connection 82 which is inserted into threaded portion 84 of passage 80 to couple liquid line 56 to housing 18. Housing 18 also is machined to include a passage 86 for interconnecting liquid inlet 80 and a liquid conduit 88. Liquid conduit 86 is closed using a threaded plug 90, and liquid conduit 88 is closed by a threaded plug 92.

FIG. 7 is a bottom plan view and FIG. 8 is an end view of the handpiece 18. FIGS. 7 and 8 illustrate a longitudinal slot 94 recessed in the bottom surface of the handpiece 18. Slot 94 is sized to receive the transducer 66 and protective cover 74. If, however, the transducer 66 and cover 74 are not received sufficiently tightly in slot 94 to hold the ultrasound transducer 66 securely therein, an additional polypropylene wedge (not shown) can be used to wedge ultrasound transducer 66 and protective cover 74 inside the slot 94.

FIG. 7 also illustrates that leading to and intersecting with the conduit 88 are plural output orifices 96a–96h. These orifices 96a–96h are fed by liquid line 56. Thus, as a conductive liquid enters the handpiece 18 through liquid line 56 and inlet 80, the conductive liquid flows through the passage 86, into passage 88 and thereafter through the plural orifices 96a–96h and onto animal 10. The spacing of these plural orifices 96a–96h is not critical. The embodiment illustrated in the figures has a relative spacing of approximately one-half inch between each respective orifice 96a–96h.

FIG. 7 also illustrates that the handpiece 18 includes plural position markings 98a–98e. As stated above, transducer 66 and protective cover 74 are positioned in slot 94. The transducer 66 and cover 74 are firmly wedged into the slot 94 and between side walls 100 and 102. A mid-portion of the transducer 66 is centered on one of these respective positioning marks 98a–98e depending upon the size of the animal, before the transducer is fixed in its selected position relative to end wall 104. More specifically, the smaller the animal, the closer transducer 66 is positioned to end wall 104 of slot 94.

II. LIVESTOCK MEASUREMENTS MADE USING THE APPARATUS

The preceding paragraphs describe one embodiment of apparatus useful for practicing the present invention. This section discusses how to operate the apparatus, with particular reference to measuring cattle.

Cattle are positioned seriatim in stall 12 during the procedure. With transducer 66 transmitting continuous ultrasound signals, operator 14 positions handpiece 18 on the back of the animal 10. The operation of the apparatus is not critically affected by the positioning of the apparatus on the back of the animal, but its positioning is important for obtaining accurate measurement data of a desired internal tissue characteristic. However, the transducer 66 preferably is positioned between the twelfth and thirteenth rib, and typically is focused on the rib-eye muscle approximately three-quarters of the way down the muscle. Once housing 18 is correctly positioned, operator 14 then actuates switch 60 to dispense a predetermined amount of conductive liquid from reservoir 52 onto the back of the animal 10. A sufficient amount of the conductive liquid is dispensed onto the animal 10 through line 56, passages 86 and 88, and orifices 96a–96h to obtain a clear image omn the monitor 20. If the monitor 20 shows that the transducer 66 is not correctly positioned, the transducer 66 can be removed from slot 94 in the handpiece 18 and repositioned. Once this is done for the first animal in a group of animals of the same type or general size, the transducer 66 will be adjusted for all animals in the group. The amount of liquid dispensed is not critical, except that there must be enough to obtain a clear signal from the ultrasound transducer 66. However, solely by way of example, less than about 50 milliliters, and more typically about 30 milliliters, of conductive liquid should suffice. Pump 36 can be actuated for particular predetermined lengths of time. The pump speed also can be controlled. The combination of controlling the pump speed and liquid dispensation time allows operator 14 to vary the amount of liquid dispensed upon animal 10 with each actuation of switch 60.

Once a suitable amount of conductive liquid is dispensed, which generally takes less than about 5 seconds, and more typically about 3 seconds, operator 14 then positions transducer 66 against the animal 10 over the oil and between the twelfth and thirteenth rib of the animal 10. The transducer 66 is held steady in this position while operator 14 views image monitor 20. Once a suitable image is obtained, operator 14 actuates trigger switch 62, which is electrically coupled to the ultrasound computer 28. By actuating switch 62, ultrasound computer 28 records the image and data, and calculates and records particular measurements of the animal 10. The data acquisition performed by ultrasound computer 28 is controlled by computer 24. Software is commercially available for running computer 24. This software can determine certain meat characteristics using the ultrasound data, including backfat, intramuscular marbling, and the area of a fat deposit. Thus, software can be selected to perform particular measurements on each animal, and measurement data obtained can be displayed on the monitor 20. If insufficient or inaccurate data is received from a reading, the animal can be remeasured. This is done by pressing reset switch 64 and again pressing trigger switch 62 to take a new reading.

The information obtained for each animal 10 is downloaded into computer 24. The animal 10 is then released from stall 12, and replaced by another. Prior to applying the transducer 66 to the back of the next animal, the operator actuates reset switch 64. This clears the computer 24 and prepares it to receive new data. The process is then repeated.

The method of the present invention takes less than about thirty seconds per animal to perform, and more typically takes only about fifteen seconds. This is a significant improvement over prior ultrasound apparatuses available for use in taking animal measurements, which typically require from about forty-five seconds to two minutes. This is an unacceptably long period of time when many animals may need to be measured daily.

The present invention has been described in accordance with a preferred embodiment. However, it will be understood that certain modifications may be made thereto without departing from the invention. I claim as my invention the preferred embodiment and all such modifications and equivalents as come within the true spirit and scope of the following claims.

I claim:

1. A system for measuring internal tissue characteristics in livestock, comprising:

a stall for positioning livestock;

a reservoir containing a conductive liquid;

an ultrasonic transducer; and a handpiece which is liquidly connected to the reservoir, the handpiece further comprising a dispenser for dispensing liquid from a reservoir onto livestock positioned in the stall.

2. The apparatus according to claim 1 further including a computer electrically coupled to the transducer.

3. The apparatus according to claim 2 and further including a liquid pump that is liquidly connected to both the reservoir and the handpiece.

4. The apparatus according to claim 3 and further including a switch unit that is liquidly coupled to both the handpiece and the pump, and electrically coupled to the transducer and the computer, the switch unit including at least a liquid switch for actuating the pump and a transducer switch for actuating the transducer.

5. The apparatus according to claim 4 wherein the switch unit further includes a computer switch for controlling computer functions.

6. The system according to claim 1, further comprising an automatic positioner for positioning the handpiece adjacent the livestock.

7. A system for measuring internal tissue characteristics in livestock, comprising:

a stall for positioning livestock;

a liquid reservoir containing a conductive liquid;

an ultrasonic transducer;

a hand-held handpiece for positioning the ultrasonic transducer adjacent livestock positioned in the stall, the handpiece further comprising a dispenser for dispensing liquid from the reservoir onto the livestock;

a liquid pump liquidly connected to both the reservoir and the dispenser; and a computer electrically coupled to the transducer.

8. The apparatus according to claim 7 and further including a switch unit that is liquidly coupled to the pump and the dispenser, and electrically coupled to the transducer and the computer, the switch unit including at least a liquid switch for actuating the pump and a transducer switch for actuating the transducer.

9. The apparatus according to claim 8 wherein the switch unit further includes a computer switch electrically coupled to the computer for actuating computer functions.

10. The apparatus according to claim 7 and further including a computer monitor that is electrically coupled to the transducer and the computer.

11. The system according to claim 7, further comprising an automatic positioner for positioning the handpiece adjacent the livestock.

12. An internal tissue measuring system for cattle, comprising:

a stall;

a reservoir containing a conductive liquid, the reservoir being positioned adjacent the stall;

an ultrasound transducer positioned adjacent the stall;

a hand-held handpiece for positioning the transducer adjacent livestock restrained in the stall, the handpiece further comprising a dispenser for dispensing conductive liquid from the reservoir and onto the livestock;

a liquid pump liquidly connected to both the conductive liquid reservoir and the dispenser; and a computer electrically coupled to the transducer.

13. The apparatus according to claim 12 and further including a switch unit that is liquidly coupled to the pump and the dispenser, and electrically coupled to the transducer and the computer, the switch unit including at least a liquid switch for actuating the pump and a transducer switch for actuating the transducer.

14. The apparatus according to claim 12 and further including a computer monitor electrically coupled to the computer and the transducer and being positioned for viewing by the operator while operating the apparatus.

15. The system according to claim 12, further comprising an automatic positioner for positioning the handpiece adjacent the livestock.

16. An internal tissue measuring system for cattle, comprising:

a stall;

a reservoir containing a conductive liquid, the reservoir being positioned adjacent the stall;

an ultrasonic transducer positioned adjacent the stall;

a hand-held handpiece for positioning the transducer adjacent livestock restrained in the stall, the handpiece further comprising a dispenser for dispensing conductive liquid from the reservoir onto the livestock;

a liquid pump liquidly connected to both the reservoir and the dispenser;

a computer for controlling the transducer; and a hand-held switch unit that is liquidly coupled to the pump and the dispenser, and electrically coupled to the transducer and the computer, the switch unit including a liquid switch for actuating the pump, a transducer switch for actuating the transducer, and a computer switch for actuating computer functions.

17. The apparatus according to claim 16 and further including a computer monitor electrically coupled to the computer and the transducer and being positioned for viewing by the operator while operating the apparatus.

18. The system according to claim 16, further comprising an automatic positioner for positioning the handpiece adjacent the livestock.

19. A method for measuring internal tissue characteristics in livestock, comprising:

positioning a live animal in a stall;

providing an ultrasound measuring apparatus comprising a reservoir containing a conductive liquid, an ultrasonic transducer, a handpiece for positioning the transducer adjacent livestock positioned in the stall, the handpiece further comprising a dispenser for dispensing conductive liquid from the reservoir onto the livestock, a liquid pump liquidly connected to both the reservoir and the dispenser, and a computer;

positioning the ultrasound transducer on an animal's hide so that the transducer is substantially focused on a rib-eye muscle;

dispensing conductive liquid from the reservoir through the dispenser and onto the hide by actuating the pump; and obtaining an ultrasound image.

20. The method according to claim 19 wherein the conductive liquid is selected from the group consisting of water, vegetable oil and mineral oil.

21. The method according to claim 19 wherein the transducer is positioned between rib 12 and 13.

22. The method according to claim 19 wherein the step of dispensing comprises dispensing a sufficient amount of the conductive liquid to increase the ultrasonic conductivity.

23. The method according to claim 22 wherein less than about 50 milliliters of conductive liquid are dispensed.

24. The method according to claim 19 and further including the step of viewing an ultrasound image on a monitor during any or all of the steps of positioning the transducer, dispensing the liquid and obtaining an ultrasound image.

25. The method according to claim 19 wherein the step of positioning the ultrasound transducer on an animal's hide comprises automated positioning.

* * * * *